(12) United States Patent
O'Rourke (10) Patent No.: US 7,628,758 B2
(45) Date of Patent: Dec. 8, 2009

(54) METHOD AND APPARATUS FOR DETERMINATION OF CENTRAL AORTIC PRESSURE

(75) Inventor: Michael F. O'Rourke, Hunters Hill (AU)

(73) Assignee: ATGor Medical Pty. Ltd., West Ryde (AU)

( * ) Notice: Subject to any disclaimer, the term of this patent is extended or adjusted under 35 U.S.C. 154(b) by 172 days.

(21) Appl. No.: 10/583,515

(22) PCT Filed: Dec. 17, 2004

(86) PCT No.: PCT/AU2004/001782

§ 371 (c)(1),
(2), (4) Date: Mar. 21, 2007

(87) PCT Pub. No.: WO2005/058155

PCT Pub. Date: Jun. 30, 2005

(65) Prior Publication Data

US 2007/0185400 A1    Aug. 9, 2007

(30) Foreign Application Priority Data

Dec. 17, 2003 (AU) .............................. 2003906952
Dec. 22, 2003 (AU) .............................. 2003907071

(51) Int. Cl.
*A61B 5/02* (2006.01)
(52) U.S. Cl. ................. 600/485; 600/481; 600/500
(58) Field of Classification Search ................. 600/485
See application file for complete search history.

(56) References Cited

U.S. PATENT DOCUMENTS

| 4,564,020 A | 1/1986 | Link |
| 5,140,991 A | 8/1992 | Niwa |
| 5,265,011 A * | 11/1993 | O'Rourke .................... 600/485 |
| 5,882,311 A | 3/1999 | O'Rourke |
| 6,010,457 A | 1/2000 | O'Rourke |
| 6,117,087 A | 9/2000 | Kamm et al. |
| 6,428,482 B1 | 8/2002 | Sungawa et al. |
| 6,612,993 B2 | 9/2003 | Narimatsu |

(Continued)

FOREIGN PATENT DOCUMENTS

JP    07-039530    2/1995

(Continued)

OTHER PUBLICATIONS

Wilkinson, Ian B., et al., "Pressure Amplification Explains Why Pulse Pressure is Unrelated to Risk in Young Subjects", Hypertension, pp. 1461-1466 (Dec. 2001).

(Continued)

*Primary Examiner*—Patricia C Mallari
(74) *Attorney, Agent, or Firm*—Andrus, Sceales, Starke & Sawall, LLP (57) ABSTRACT

Methods for determining central systolic pressure are disclosed. A first method determines the time of peak in a measured carotid waveform and then determines the pressure in a measured radial waveform at the corresponding time. A second method utilises only a measured radial waveform. The waveform is analysed to determine a time indicative of lower body waveform and determines the pressure at this time. In each case, the determined pressure is substantially the same as the central systolic pressure.

11 Claims, 7 Drawing Sheets

U.S. PATENT DOCUMENTS

| | | |
|---|---|---|
| 6,616,613 B1 | 9/2003 | Goodman |
| 6,647,287 B1 | 11/2003 | Peel, III et al. |
| 6,740,045 B2 | 5/2004 | Amano |
| 7,144,373 B2 | 12/2006 | Sato et al. |
| 2002/0177781 A1* | 11/2002 | Amano ................... 600/485 |
| 2004/0167414 A1 | 8/2004 | Tanabe et al. |
| 2005/0283087 A1 | 12/2005 | Takazawa et al. |

FOREIGN PATENT DOCUMENTS

| | | |
|---|---|---|
| JP | 2002-051995 | 2/2002 |
| JP | 2003-000555 | 1/2003 |
| JP | 2004-222847 | 8/2004 |

OTHER PUBLICATIONS

"Development and Comparative Analysis of Algorithms for Derivation of Central Aortic Pressure From the Peripheral Arterial Pulse", Thesis of Ahmad Al Haj Qasem, Jan. 2002.

* cited by examiner

Pressure Waveform Type 1

1st Derivative

2nd Derivative

3rd Derivative

Fig 4b

Pressure Waveform Type 2

1st Derivative

2nd Derivative

3rd Derivative

Fig 4c

Pressure Waveform Type 3

1st Derivative

2nd Derivative

3rd Derivative

Fig 4d

Pressure Waveform Type 4

1st Derivative

2nd Derivative

3rd Derivative

Fig 4e

Pressure Waveform Type 5

1st Derivative

2nd Derivative

3rd Derivative

METHOD AND APPARATUS FOR DETERMINATION OF CENTRAL AORTIC PRESSURE

FIELD OF THE INVENTION

The present invention relates to the determination of central aortic systolic and pulse pressure from a peripheral waveform.

BACKGROUND OF THE INVENTION

The relationship between systolic blood pressure in the arm and cardiovascular events is well established, and is the basis for modern therapy for hypertension. Such therapy, aimed at reducing brachial systolic pressure, has been very successful in reducing death and disability from cardiovascular events.

However, the brachial systolic and pulse pressure may differ significantly from the corresponding values in the aorta and central arteries. Measurements of central aortic systolic and pulse pressure have been demonstrated as superior to brachial pressure in correlating with severity of existing disease and prediction of subsequent events. Such studies have used direct pressure measurements during cardiac catheterization, or estimates of pressure from the carotid pressure or diameter waveform. Another measurement approach is described in U.S. Pat. No. 5,265,011 to O'Rourke, whereby central systolic and pulse pressure can be determined from a peripheral pressure waveform using a transfer function.

Whilst the latter method has proved highly successful in practice, it requires reasonably complex processing. In order to enable the determination of central aortic systolic and pulse pressure from a peripheral site, using a relatively simple instrument, it would be advantageous to provide a simpler method requiring a less sophisticated processing approach.

SUMMARY OF THE INVENTION

According to a first aspect of the present invention there is provided a method for determining central systolic pressure, comprising the steps of:

determining a time t from pressure wave foot to peak in a central carotid artery;

measuring a radial pressure waveform; and locating the pressure wave foot in the radial pressure waveform and determining the corresponding pressure at time t after the wave foot;

wherein said corresponding pressure is substantially the central systolic pressure.

According to a second aspect of the present invention there is provided a method for determining central systolic pressure, comprising the steps of:

measuring a radial pressure waveform;

locating the time of start of a component of said waveform attributable to lower body wave reflection; and determining the central systolic pressure by taking the value of the pressure waveform at said time.

Preferably, the start of the component attributable to lower body wave reflection is determined by analysing the waveform to locate the inflection in the waveform attributable to lower body reflection.

Preferably, the methods can be implemented in software for programming an apparatus to carry out the methods.

The present invention was derived from careful consideration of the underlying processes. In human adults, under normal conditions, the peak of the aortic pressure wave is usually in late systole, some 150 ms or more after initial upstroke of the pulse. In contrast, the peak of the pressure wave in the upper limb usually occurs much earlier, some 90-130 ms after the initial upstroke of the wave. The difference in waveform between the two sites is attributable to differences in timing of wave reflection in the lower body and upper limb. The aortic peak is largely due to the later return of wave reflection from the distant lower body, whereas the upper limb peak is due to summation of early reflected waves from within the upper limb itself. Recognition of such differences lead to the present invention.

A practical advantage of the present invention is that it allows for relatively accurate determination of the central aortic systolic pressure without requiring the application of a transfer function or a similar complex technique.

BRIEF DESCRIPTION OF DRAWINGS

Implementations of the present invention will now be described with reference to the accompanying drawings, in which.

DESCRIPTION OF PREFERRED EMBODIMENTS

The present invention will be described with reference to illustrative embodiments. It will be appreciated that the invention is not confined to any particular physical implementation.

In the present invention, the pulse pressure is determined in the same manner as systolic pressure, but is calculated as the systolic pressure minus the diastolic pressure, so as to give the amplitude of the wave. Consequently, the exemplary system of the present invention preferably comprises means for calculating the pulse pressure from tonometer measurements and the calculated central systolic pressure wave, such as a simple processor having computer software loaded therein for carrying out the calculations.

Figure 1:
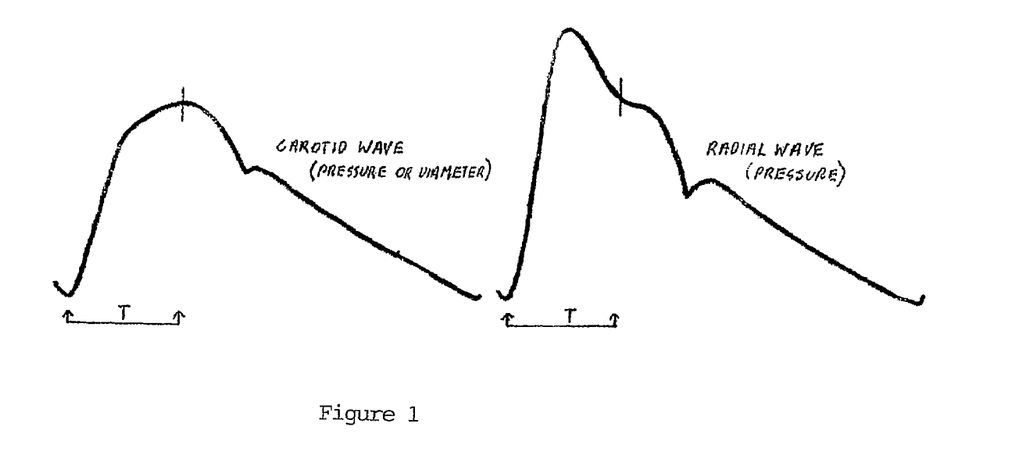
FIG. 1 illustrates the waveforms associated with an exemplary implementation of the first aspect of the present invention.

An exemplary implementation of the first aspect of the present invention requires the measurement of both the carotid and radial pressure waveforms in order to determine the central (aortic) systolic pressure. FIG. 1 shows pressure waveforms measured non-invasively from the carotid artery and from the upper limb. The upper limb waveform is measured, for example, at the radial artery. Time t is shown, representing the time from wave foot to peak in the carotid waveform. At this time t from the foot of the radial waveform, the initial peak has passed and the waveform shows the broad peak associated with the lower body reflections. The pressure value at this time in the radial waveform is a close approximation to the systolic pressure value in the aorta. The radial waveform is calibrated using, for example, conventional brachial cuff techniques.

It will be understood that determining the time t from the wave foot to peak is a simple matter of determining the time from minimum to maximum value, which can be readily captured by a simple digital system. The time t can then be applied to a captured data set of pressure against time, in order to find the pressure time t after the minimum value in the radial waveform. A practical implementation is straightforward for a suitably skilled electronic engineer. Display of the radial or carotid waveforms is not required.

Accordingly, this implementation of the first aspect of the present invention relies on locating the broad peak using timing information from central (carotid) arteries and detecting the radial pressure value where it corresponds to the central pressure. It will be appreciated that this method requires measurement of pressure or diameter in a central artery, in order to acquire the timing information, and this measurement is ideally made under similar conditions to the radial tonometry. Any suitable sensing arrangement may be used, provided a sufficiently accurate timing can be extracted.

On the other hand, an exemplary implementation of the second aspect of the present invention only requires measurement of the brachial or radial waveform in order to determine the central (aortic) systolic pressure. Specifically, this implementation excludes the effects of wave reflection in the upper limb and identifies the reflected wave from the lower body, which normally comprises the peak of pressure in the ascending aorta.

This is accomplished by analysing derivatives of the upper limb pressure waveform, so as to identify the peak of the pressure wave which returns from the lower body, and which constitutes the late systolic surge of pressure after the initial peak. The time T2 denotes the peak of this wave. Brachial or radial pressure at T2 is peak aortic systolic pressure (ASP) and aortic pulse pressure is ASP minus brachial or radial diastolic pressure.

Figure 3:
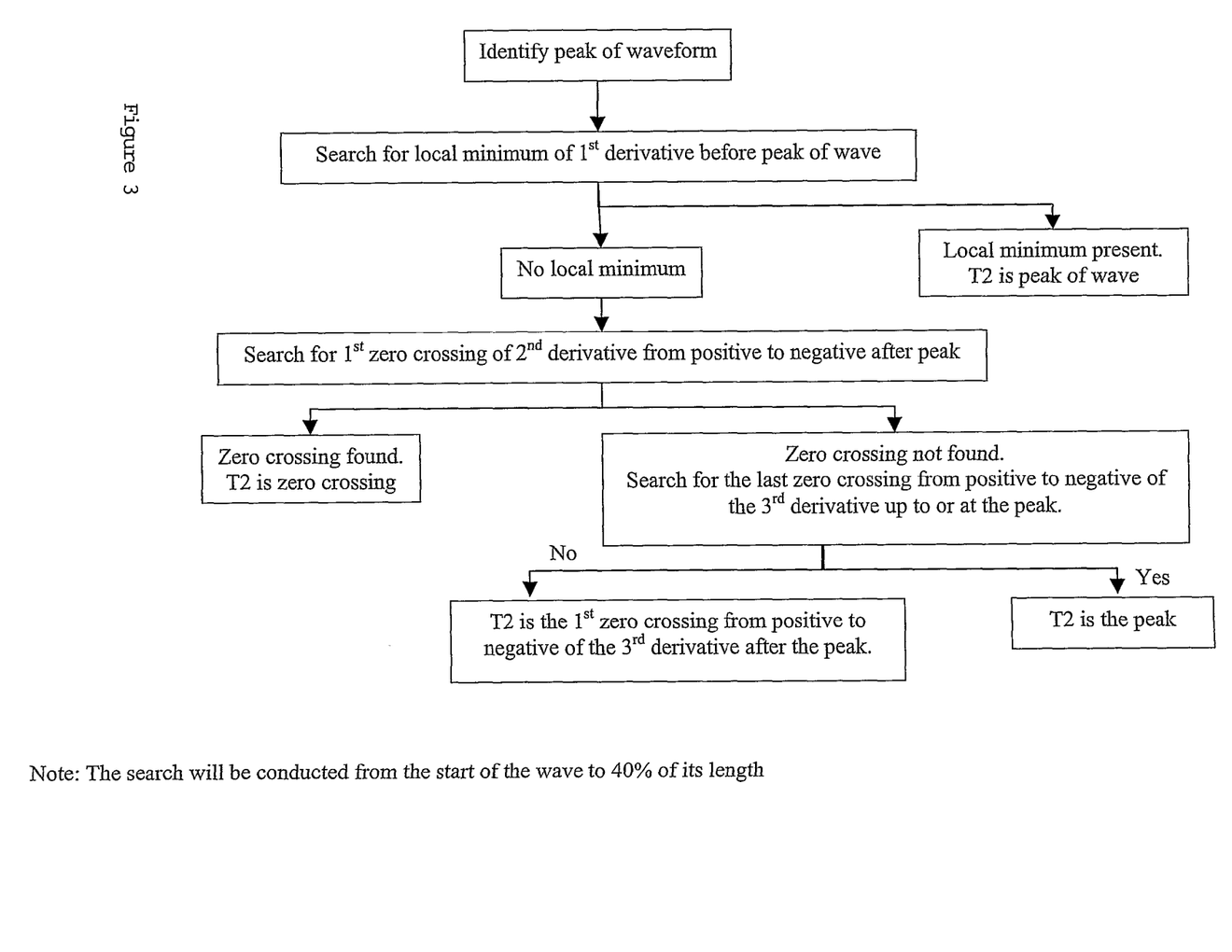
FIG. 3 illustrates a flow chart of an exemplary implementation of the second aspect of the present invention.
Figure 4A:
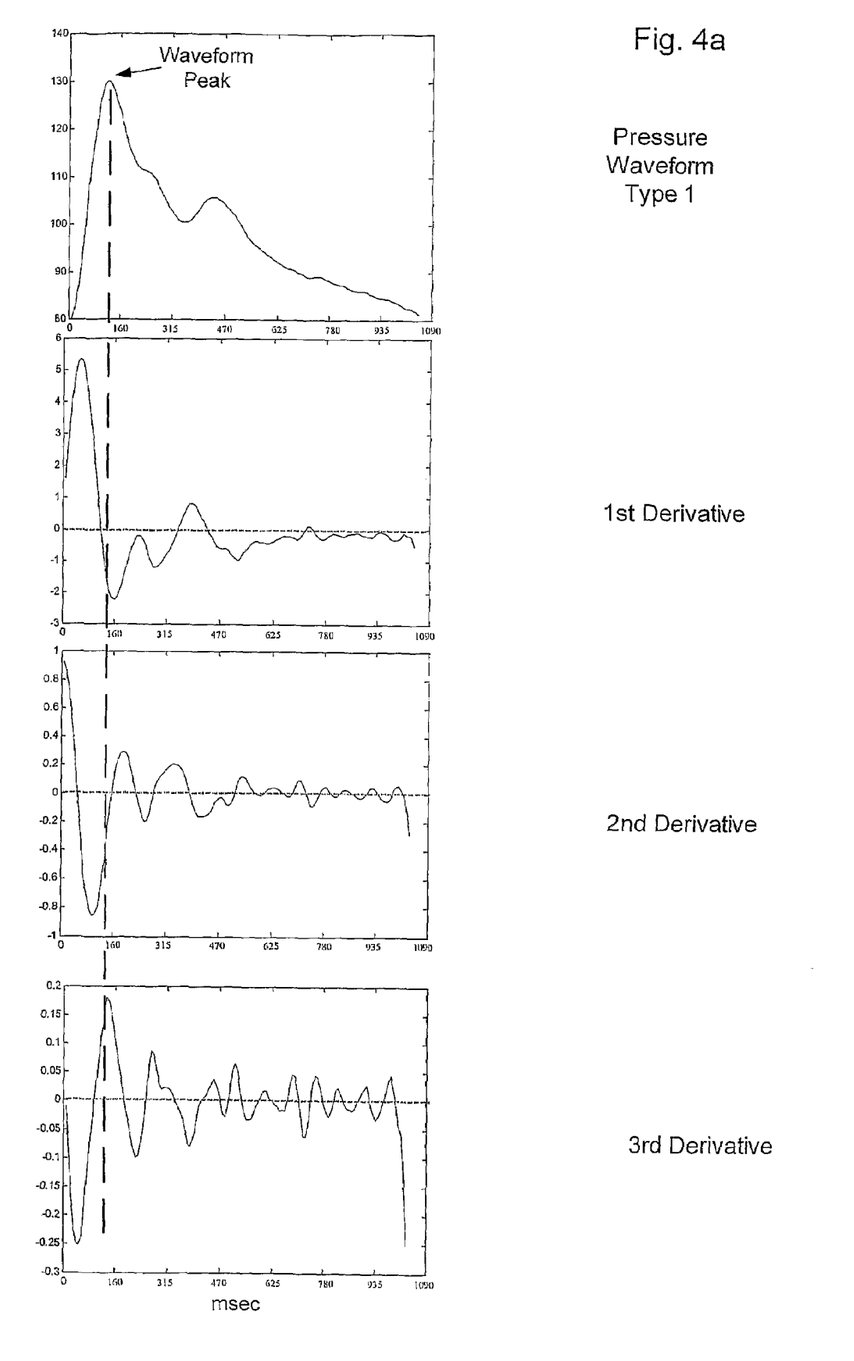
FIGS. 4a to 4e illustrate variants of radial artery waveforms associated with the method illustrated in FIG. 3.
Figure 4B:
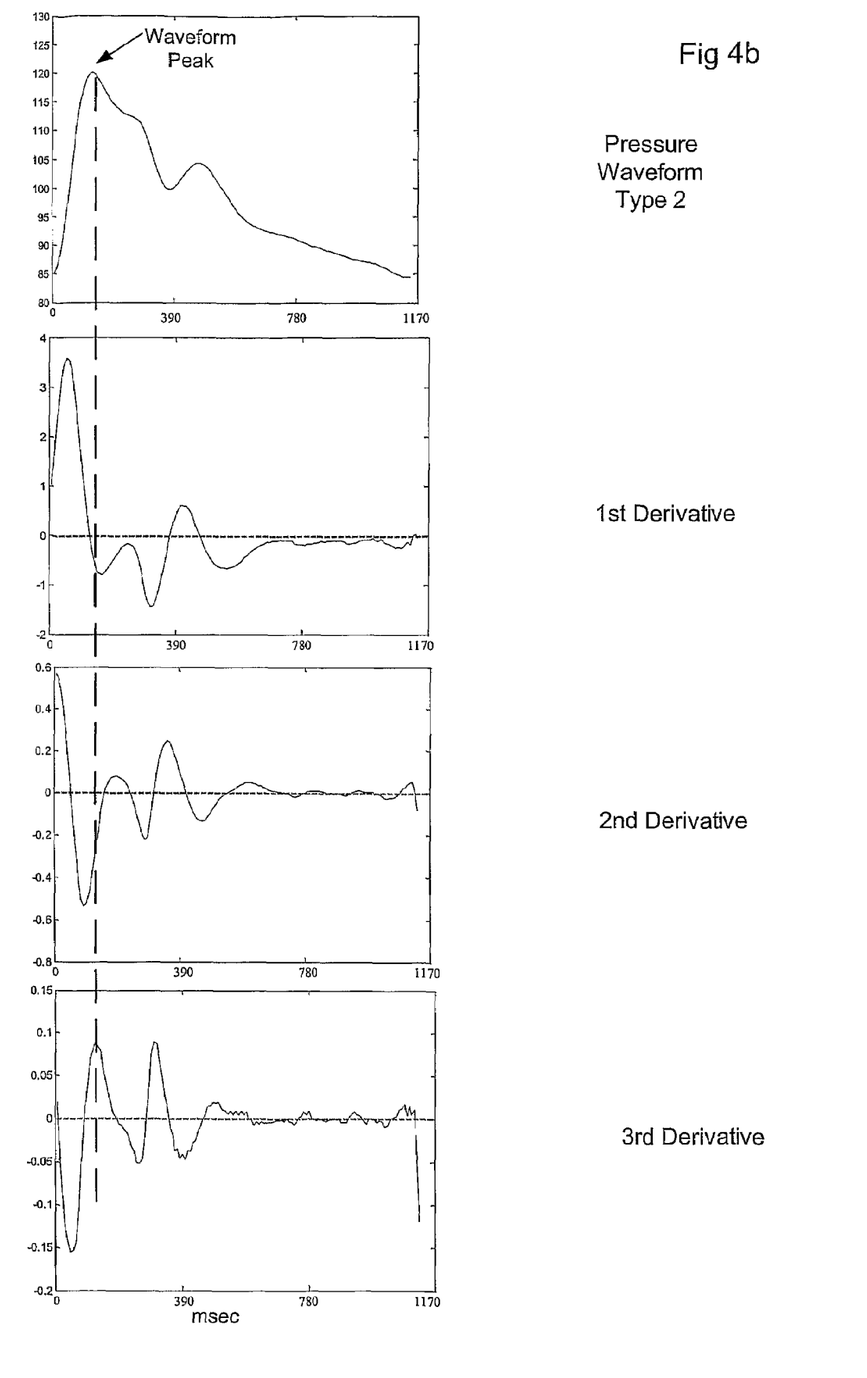
Figure 4C:
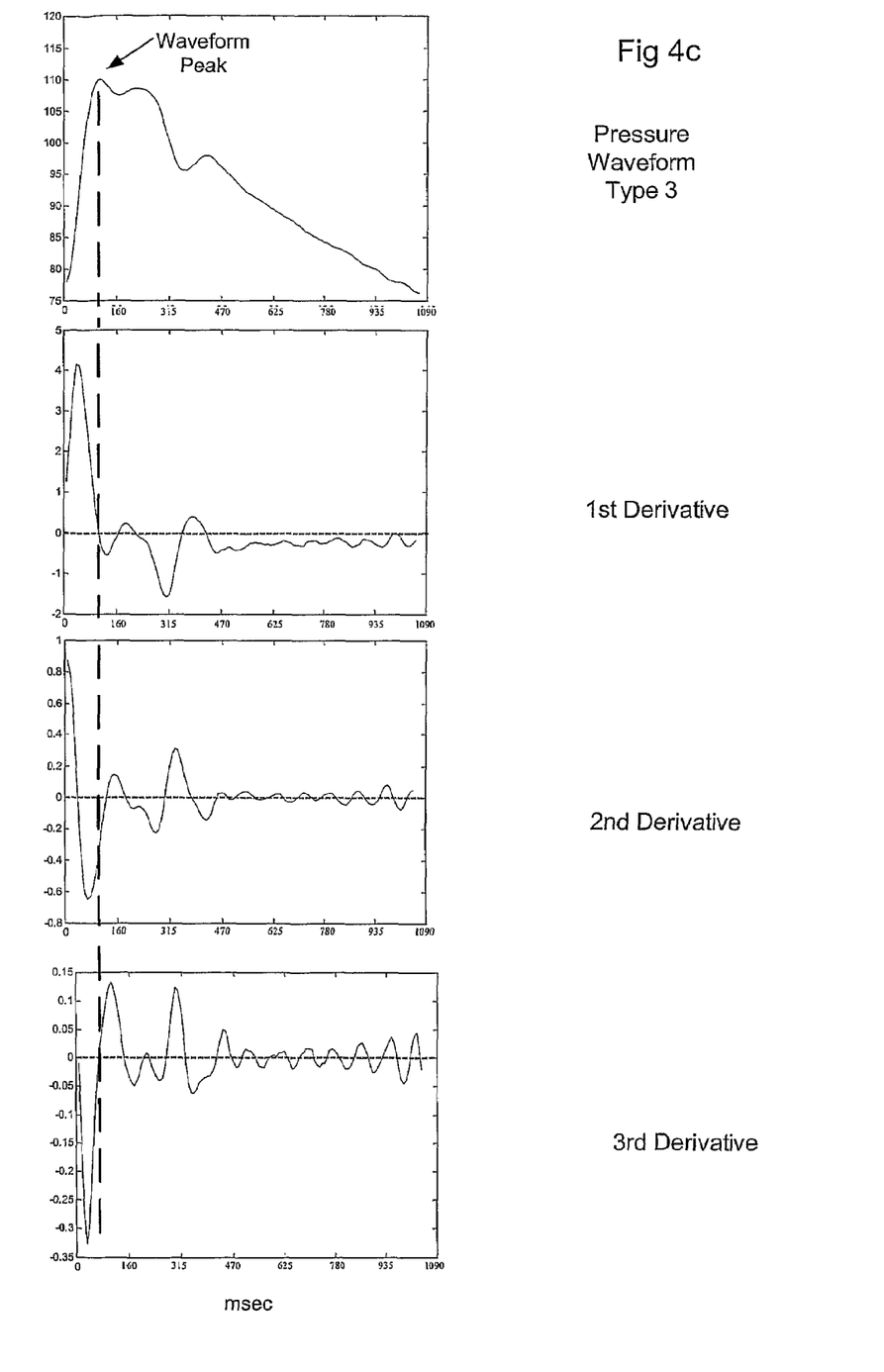
Figure 4D:
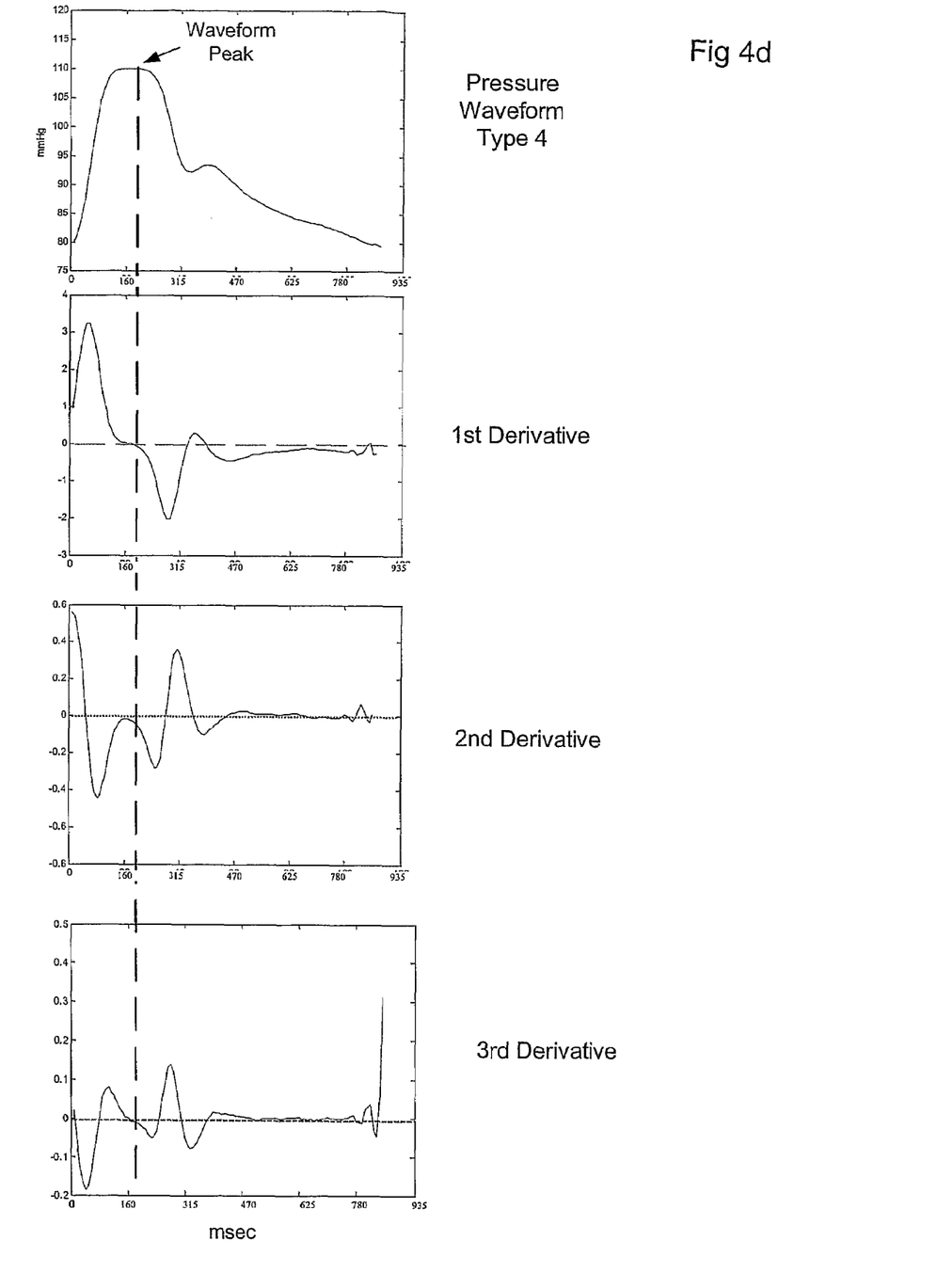
Figure 4E:
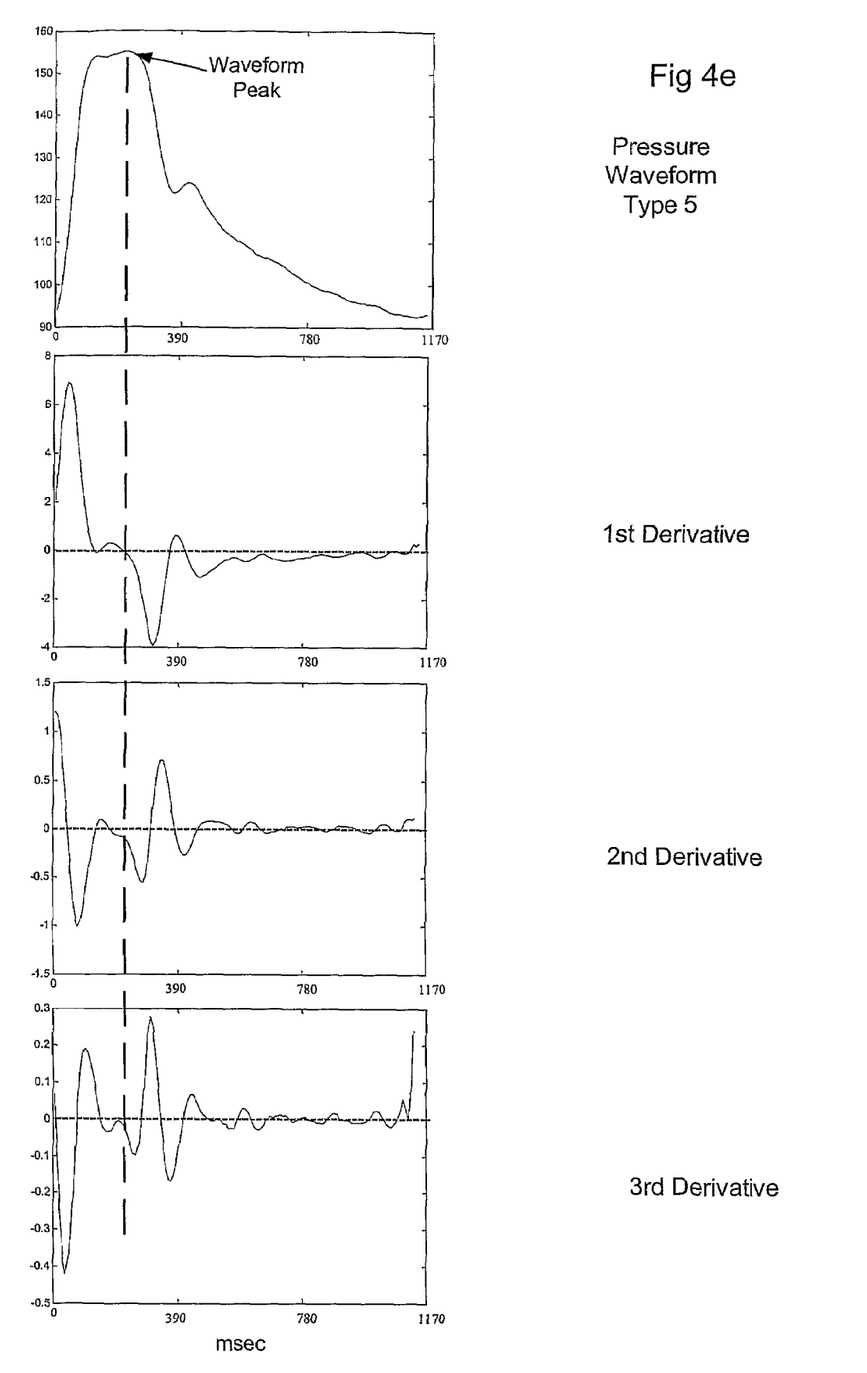

The first, second and third derivatives of upper limb the pressure wave are analysed for this purpose, as outlined in the flowchart in FIG. 3. First, the peak of the waveform is identified. Then a search is conducted for any local minimum of the first derivative before the peak of the recorded pressure wave. If a local minimum of the first derivative is present, then T2 is set at the peak of the recorded wave, and this is taken to represent peak aortic systolic pressure; when this occurs the pressure peak is generated well after peak flow in the artery, and so more than 150 msec after the wave foot. Ideally, the local minimum of the first derivative is detected by determining whether there is a zero crossing from negative to positive in the second derivative.

Figure 2:
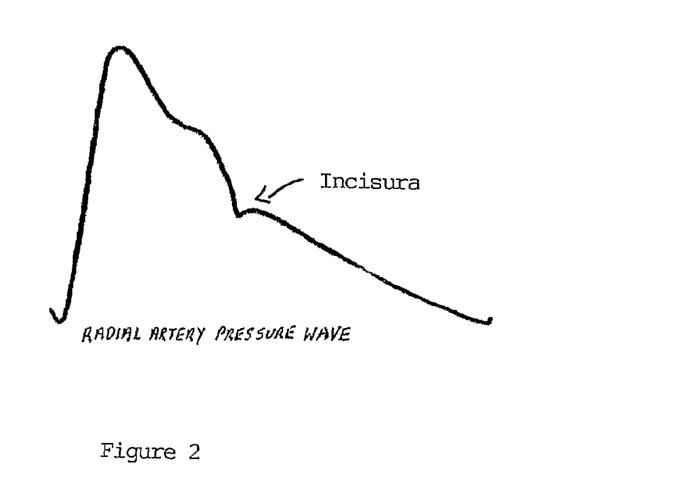
FIG. 2 illustrates an example radial artery pressure waveform.

If there is no localised minimum of the first derivative before the peak of the wave, then there is a search for the first zero crossing from positive to negative of the second derivative after the peak of the recorded wave and before the incisura. If there is a zero crossing, then this is taken to represent T2 and pressure of the recorded wave at this point is taken to represent peak aortic systolic pressure. There will always be a zero crossing at the time of incisura (that is, at the beginning of diastole). As shown in FIG. 2, the incisura normally occurs quite late in the waveform (more than 250 ms after the initial wavefoot, well after peak flow in the artery, and hence it is necessary to exclude the incisura from being detected. Thus the search for the zero crossing can be practically restricted to within the first 40% of the waveform.

If the second derivative shows no zero crossing from positive to negative after the peak of the wave, then there is a search for the last zero crossing from positive to negative of the third derivative up to or at the peak of the recorded wave. If there is a zero crossing, then T2 is set at the peak of the recorded wave. If there is no zero crossing, then there is a search for the first zero crossing from positive to negative of the third derivative after the peak of the recorded wave and T2 is set at the time of this zero crossing and the pressure of the recorded wave at this point is taken to represent peak aortic systolic pressure.

The application of this process is shown in the five recorded radial artery pressure waveforms in FIG. 4. As can be seen, for each of waveforms 1, 2 and 3 a secondary systolic or reflected wave is apparent in the upper limb. In these three waveforms, the time T2 (at which radial artery pressure approximates aortic peak pressure) occurs after the peak of the recorded wave and is identified from the second differential. In the waveform 5, the peak of the wave occurs in late systole and is preceded by a local minimum of the first derivative. The peak constitutes T2 and the peak pressure approximates that in the aorta. In waveform 4, there is no apparent separate reflected wave in the upper limb, but the peak of the pressure wave occurs more than 150 msec after the foot of the wave, and the third derivative shows a localised zero crossing. For waveforms 4 and 5, peak pressure occurs more than 150 msec after the wave foot, while for waveforms 1, 2 and 3, the peak occurs earlier than 150 msec, and corresponds to the peak of flow in the artery.

The above described processor may preferably determine whether the differentials need to be calculated based on the determination of the timing of a reflected wave, and returns the aortic systolic pressure value accordingly.

It will be appreciated that variations and additions are possible within the spirit and scope of the invention.

The invention claimed is:

1. A method for determining central systolic pressure, comprising the steps of:
   determining a time t from a pressure wave foot to a peak in a central carotid artery;
   measuring an upper limb pressure waveform with a sensor; and
   using a computer program embodied on a computer readable medium to locate the wave foot in the upper limb pressure waveform and determine the corresponding pressure at time t after the wave foot;
   wherein said corresponding pressure is substantially the central systolic pressure.

2. A method for determining central systolic pressure, comprising the steps of:
   measuring an upper limb pressure waveform with a sensor;
   using a computer program embodied on a computer readable medium to locate a time of the start of a component of said upper limb pressure waveform attributable to lower body wave reflection by analyzing derivatives of the upper limb pressure waveform; and
   using a value of the upper limb pressure waveform at said time in the computer program to determine the central systolic pressure.

3. The method according to claim 2, wherein said step of locating the time comprises the following steps:
   determining a peak of said upper limb pressure waveform;
   determining if there is a minimum of a first derivative of said upper limb pressure waveform before said peak;
   if a minimum is determined then treating the time as being located at the occurrence of said peak;
   if no minimum is determined then:
   searching for a first zero crossing of a second derivative of said upper limb pressure waveform from positive to negative after said peak and before incisura;
   if a first zero crossing is found then treating the time as being located at said first zero crossing;
   if a first zero crossing is not found then:

searching for a zero crossing of a third derivative of said upper limb pressure waveform from positive to negative before said peak;

if a zero crossing is found then treating the time as being located at the occurrence of said peak;

if a zero crossing is not found then:

searching for a first zero crossing of the third derivative from positive to negative after said peak and treating the time as being at said zero crossing.

4. The method according to claim 3, wherein said step of determining if there is a minimum of a first derivative of said upper limb pressure waveform before said peak comprises determining if there is a zero crossing of a second derivative from negative to positive before said peak.

5. A computer-readable medium having a computer-readable program for programming a device to determine the central systolic pressure according to the method of claim 1.

6. A computer-readable medium having a computer-readable program for programming a device to determine the central systolic pressure according to the method of claim 2.

7. The method as recited in claim 1 wherein the measured upper limb pressure waveform is a radial pressure waveform measured using a tonometer.

8. A method as recited in claim 2 wherein the measured upper limb pressure waveform is a radial pressure waveform measured using a tonometer.

9. The method as recited in claim 1 wherein the measured upper limb pressure waveform is a brachial pressure waveform.

10. A method as recited in claim 2 wherein the measured upper limb pressure waveform is a brachial pressure waveform.

11. A method as recited in claim 2 further comprising the step of limiting the search for the time of the start of the component of the upper limb pressure waveform attributable to the lower body wave reflection to an initial 40% of the length of time of the upper limb pressure waveform after the wave foot for the waveform.

* * * * *

UNITED STATES PATENT AND TRADEMARK OFFICE
CERTIFICATE OF CORRECTION

PATENT NO. : 7,628,758 B2 Page 1 of 1
APPLICATION NO. : 10/583515
DATED : December 8, 2009
INVENTOR(S) : Michael F. O'Rourke

It is certified that error appears in the above-identified patent and that said Letters Patent is hereby corrected as shown below:

Title Page [73] Assignee:

Delete "ATGor Medical Pty. Ltd.," and substitute therefor --AtCor Medical Pty. Ltd.--

Signed and Sealed this

Twenty-seventh Day of April, 2010

David J. Kappos
*Director of the United States Patent and Trademark Office*